US007089062B1

(12) United States Patent
Yamada

(10) Patent No.: US 7,089,062 B1
(45) Date of Patent: Aug. 8, 2006

(54) PULSE WAVE APPLICATION SYSTEM

(75) Inventor: Taketoshi Yamada, Tokyo (JP)

(73) Assignee: Kabushiki Kaisha Wado Doctors Group, Tokyo (JP)

( * ) Notice: Subject to any disclaimer, the term of this patent is extended or adjusted under 35 U.S.C. 154(b) by 468 days.

(21) Appl. No.: 10/111,732

(22) PCT Filed: Oct. 30, 2000

(86) PCT No.: PCT/JP00/07632

§ 371 (c)(1),
(2), (4) Date: Nov. 27, 2002

(87) PCT Pub. No.: WO01/30298

PCT Pub. Date: May 3, 2001

(30) Foreign Application Priority Data

Oct. 29, 1999 (JP) ................................ 11-310231

(51) Int. Cl.
*A06N 1/32* (2006.01)

(52) U.S. Cl. ........................................................ 607/68

(58) Field of Classification Search .................. 607/68, 607/69, 70, 71, 72

See application file for complete search history.

(56) References Cited

U.S. PATENT DOCUMENTS 4,503,863 A * 3/1985 Katims ........................ 600/554
4,646,744 A * 3/1987 Capel .......................... 607/58
5,107,835 A * 4/1992 Thomas ....................... 607/46
5,342,410 A * 8/1994 Braverman .................. 607/58
6,154,669 A * 11/2000 Hunter et al. ............... 600/383

FOREIGN PATENT DOCUMENTS

CN 1026466 C 11/1994
CN 1030134 C 10/1995
EP 0909568 A2 4/1999
JP 3-77560 * 4/1991
JP 7-289649 * 11/1995
JP 10-108913 * 4/1998
JP 11-151302 * 6/1999

OTHER PUBLICATIONS

Chinese Office Action dated Oct. 10, 2003 for the Chinese Patent Application corresponding to the U.S. patent application, including English translation.

* cited by examiner

*Primary Examiner*—Robert E. Pezzuoto
*Assistant Examiner*—Jessica L. Reidel
(74) *Attorney, Agent, or Firm*—Intellectual Property Law Group LLP; Otto O. Lee; Juneko Jackson

(57) ABSTRACT

The output state of a pulse wave optimum to the user and applied to the head of the user is automatically set while improving the wearability of the electrodes, and different output states of pulse waves can be simultaneously applied to a large number of users. A pulse wave of predetermined pattern is given to the skin near an ear of the user and/or of the back of a hand of the user to directly stimulate and activate the brain. This stimulation is significantly effective especially for colorblindness. By systematizing such a revolutionary therapy, pulse waves of different patterns can be applied to a large number of patients (users), enabling a quick, effective therapy.

8 Claims, 6 Drawing Sheets

22 20 12 26 28 16 20 22 Pulse Wave Output 26A 30 28A 30 26 28 18 32

24
CR OSCILLATOR (OP AMPLIFIER)
40
O
SWITCHING CIRCUIT
38
CONSTANT CURRENT CIRCUIT
50
RELAY CONTACT
52
32
OUT
RING COUNTER (SCALE-OF-4 RING COUNTER OR SCALE-OF-N RING COUNTER)
42
A
B
C
D
CLOCK CIRCUIT
44
CLK
RES
ONE-SHOT CIRCUIT
46
F/F CIRCUIT
48
36
54
RLY
V1
V3
V1
POWER SUPPLY CIRCUIT
34
AC100V 50/60Hz

PULSE WAVE APPLICATION SYSTEM

CROSS-REFERENCE TO RELATED APPLICATIONS

This application is the National Stage of International Application No. PCT/JP00/07632, filed Oct. 30, 2000, and claims benefit of Japan application no.: 11/310231, filed Oct. 29, 1999.

BACKGROUND OF THE INVENTION

1. Field of the Invention

The present invention relates to a system for applying pulse waves to a human body. Specifically, this invention relates to a system for applying pulse waves particularly to the head of the human body in order to enhance and improve the activity level of the nervous system, particularly the cranial nerve of the human body. More specifically, it is an application system designed to enhance and recover the activity level of the brain by putting electrodes on both ears of the human body and applying the pulse waves between the electrodes through the human body. This invention relates to an application system which can improve and solve various malfunctions and defects relating to the cranial nerve, for example, congenital intelligence impairment (such as Down syndrome), acquired intelligence impairment (such as senile dementia and serious depression), or colorblindness, and which can also enhance and improve intellectual levels such as EQ and IQ of a physically unimpaired person.

2. Description of the Related Art

The applicant developed a method of improving abnormal color sensation of a human body such as anomalous trichromatism and colorblindness by using electric signals, and has achieved desirable effects. The conventional method is to put electrodes on the head of the human body, particularly on both ears, and apply a specific electric pulse signal between the pair of electrodes by means of an application control device. Specifically speaking, a user holds the pair of electrodes with his/her hands respectively and maintains the state in which the electrodes are put on the corresponding ears. The pair of electrodes is contained in pads and the electrode surfaces are covered with sponges soaked in a solution. In other words, the pair of electrodes contacts the user's ears through the sponges. Therefore, an electric signal is applied between both ears.

The applicant discovered from many years of study that application of specific electric signals to the head of the human body can improve abnormal color sensation such as anomalous trichromatism and colorblindness and metabolic disorders such as allergies.

In recent years, for example, senile dementia has become a significant social issue, but curative medicines for senile dementia are limited in their effects. It can be considered that symptoms such as the colorblindness and the senile dementia are attributed to occurrences of dysfunction in the functioning of the central nervous system such as the brain, or impairment of such functioning or an insufficient state of the functioning.

It is an object of the present invention to provide an application system for a human body, which can enhance, improve or ameliorate the comprehensive activity level of the cranial nerve and the central nervous system. Another object of the present invention is to provide an application system for the human body, which can improve abnormal color sensation and also improve and solve senile dementia and congenital intelligence impairment. Still another object of the present invention is to provide an application system for the human body, which can enhance the mental activity level and the intellectual level, such as EQ and IQ, of a physically unimpaired person.

A further object of the present invention is to provide a system which achieves activation of the entire nervous system of the human body, and further to provide an application system which activates the motor nerve to enhance athletic ability.

SUMMARY OF THE INVENTION

After dedicated research, the inventor discovered that in order to achieve the above-described objects, it is preferable that characteristics of pulse wave signals be changed periodically or regularly when applying the pulse waves to the head of the human body. It is effective to provide a pulse wave signal from both ears of the head of the human body. For example, a pair of electrodes for applying the pulse wave is connected to a pulse wave generating unit to provide the pulse wave to the head through the pair of electrodes.

The present invention is a pulse wave application system for applying a pulse wave to a human body, comprising: a pulse wave output controlling unit for generating pulse wave signals and changing characteristics of the generated pulse wave signals periodically; and a pair of electrode units, to which the pulse wave signal is supplied, wherein the electrode units are placed on the head of the human body to apply the pulse wave thereto. It is preferable that the electrode units be structured in such a manner that they can be put on the ears of the head of the human body.

According to one embodiment of the present invention, the controlling unit either outputs a pulse wave having a relatively high frequency and a pulse wave having a relatively low frequency alternately or outputs the pulse wave in such a manner that its frequency gradually becomes higher or lower. The controlling units also repeat the output states of the pulse wave periodically and changes the polarity of the pulse wave periodically.

According to another embodiment of the present invention, a client connected to a communication network is provided with the pulse wave output controlling unit and the controlling unit outputs a pulse wave signal on the basis of a control signal which is supplied from a server to the client.

As described above, in the application of the pulse wave, it is effective to change or repeat the characteristics of the pulse wave at certain intervals, instead of maintaining constant characteristics. The application may be conducted by alternately applying plural kinds of pulse waves having characteristics different from one another to the electrodes.

A more specific embodiment of the present invention is a pulse wave application system having a pulse wave output controlling unit connected to a communication terminal, in which the pulse wave output controlling unit outputs, by using a communication line, a pulse wave which is controlled by a pulse wave generation program stored in the communication terminal. In this pulse wave application system, the pulse wave output controlling unit is structured to apply plural kinds of pulse waves between a pair of main electrodes, which can be put on certain positions on the head.

The pulse wave output unit controls the characteristics and manner of the output pulse waves and determines to what extent these pulse waves are continuously applied. Accordingly, it is possible to output plural kinds of pulse waves by combining them. Moreover, the polarities of the pulse waves applied to the pair of electrodes can be switched.

The output state of the pulse wave outputted by the pulse output controlling unit and parameters for deciding the output state are entered into a database by establishing correspondences between them. The output state of the pulse wave is automatically set by inputting the parameters.

When deciding the output state of the pulse wave, the status of a user needs to be recognized. At this time, a necessary parameter is prepared and the parameter is decided according to the status of the user, thereby providing a database in which the parameter is associated with the output state of the pulse wave. Accordingly, the output state of the pulse wave can be set automatically.

Moreover, the system is characterized in that the pair of main electrodes is put on both ears of the human body or the peripheral areas thereof. A pair of subelectrodes that can be put on the human body, other than on the head may be provided.

If the pair of subelectrodes which can be put on the human body except on the head, is provided in addition to the main electrodes and is used as appropriate, the effects of the pulse wave can be enhanced.

The pulse wave output controlling unit is connected to plural pairs of main electrodes and/or subelectrodes. The main electrodes and/or subelectrodes are divided into groups of those having the same output states of pulse waves outputted by the pulse wave controlling unit, and plural pulse wave applications are conducted simultaneously.

For example, by connecting plural pairs of main electrodes and/or subelectrodes to a single pulse wave output controlling unit, it is possible to conduct the pulse wave application on plural persons simultaneously. Moreover, these main electrodes and/or subelectrodes are divided into groups and the pulse waves are applied in a different output state for each group. Accordingly, it is possible to gather users under different conditions and conduct the treatments simultaneously. Therefore, the pulse wave application can be completely systematized.

DESCRIPTION OF THE PREFERRED EMBODIMENTS

Figure 1:
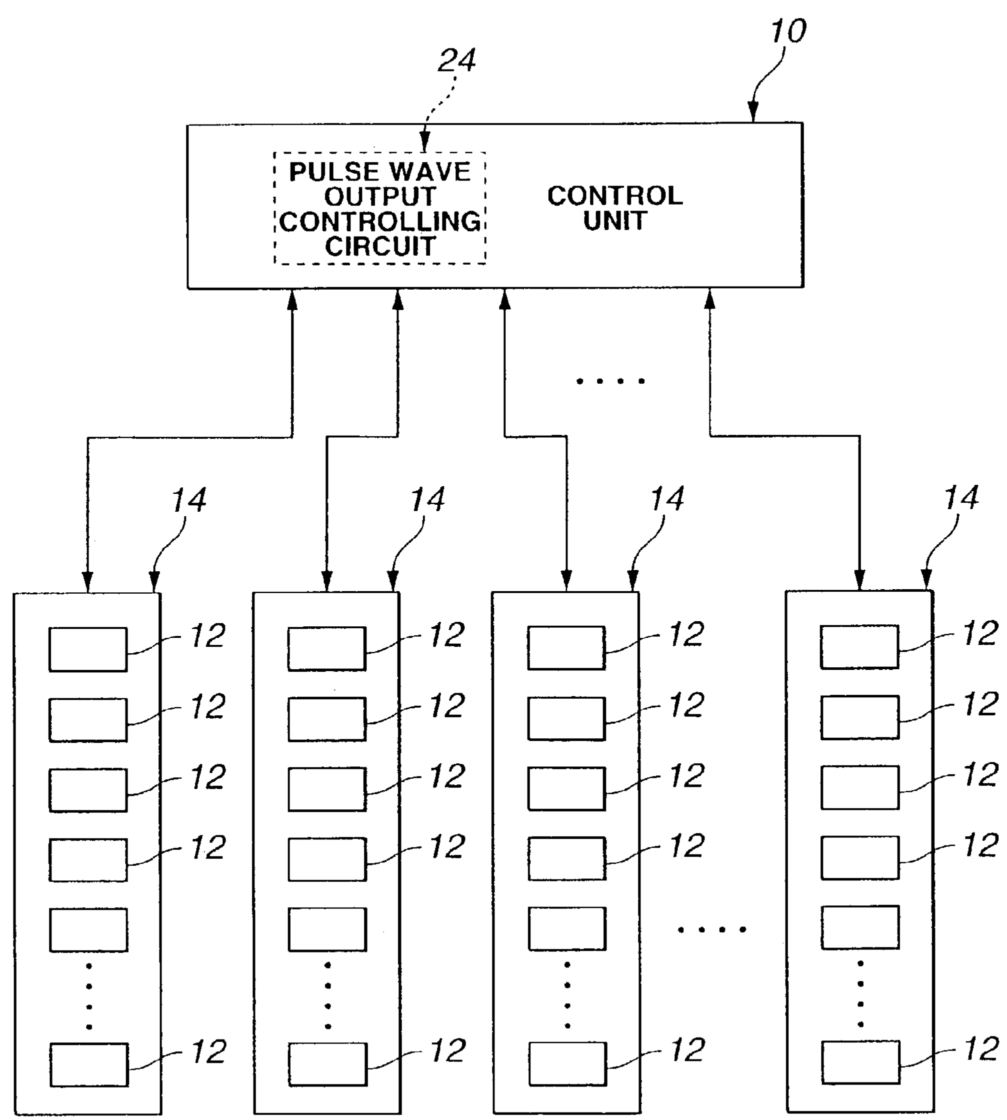
FIG. 1 is a schematic block diagram of the pulse wave application system according to an embodiment of this invention.

FIG. 1 is the schematic diagram of the pulse wave application system. The pulse wave application system comprises a control unit 10 for controlling the output state of the pulse wave, and plural booths 14 respectively connected to the control unit 10 and having plural operation tables 12 (see FIG. 2) for conducting the pulse wave application.

Figure 2:
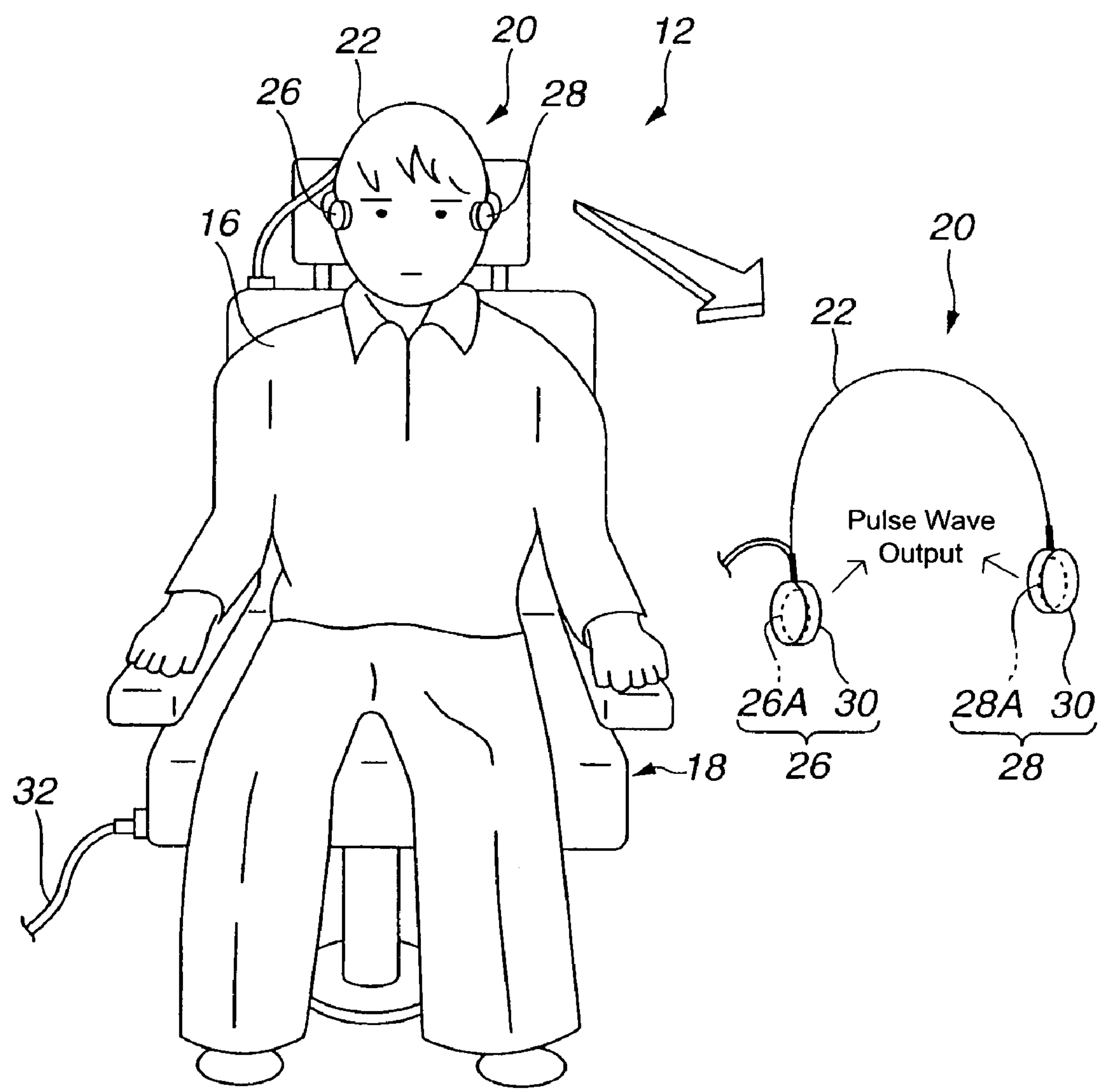
FIG. 2 is a detailed view of a treatment table.

As shown in FIG. 2, the operation table 12 is structured in a manner that a chair 18, on which a user 16 is seated, has a head set 20 formed in a shape of a head phone attached to the chair 18. The head set 20 comprises an elastic bridge member 22 and a pair of electrodes 26 and 28 attached to the bridge member 22 for supplying the pulse wave outputted from the pulse wave output controlling circuit 24 (see FIGS. 1 and 3), which will be described later, to the human body.

The pair of electrodes 26 and 28 is structured in a manner that carbon electrode agents 26A and 28A are covered with sponges 30 containing an application solution, and the entire shape of each electrode is a thin disk. This pair of electrode 26 and 28 is directly put on both ears when the user 16 puts the bridge member 22 on his/her head.

A wire 32 to the pair of electrodes 26 and 28 is connected to the control unit 10 (see FIG. 1) either directly or through the inside of the chair 18. Various sensors (not shown in the drawing) for detecting the user's heart rate, pulse, blood pressure, brain wave, and so forth may be mounted on the operation table 12. The detection results by the sensors may be inputted in the control unit 10 so as to be collectively managed and used as one of the parameters for determining the output state of the pulse wave for medical treatment.

The plural booths 14 (see FIG. 1) are designed in a manner that different pulse waves can be outputted from the pairs of electrodes 26 and 28 for each unit. Users are divided into groups of those receiving the pulse waves of the same condition, and sorted out into respective booths 14. Accordingly, it is possible to conduct the simultaneous treatments (supply of the pulse waves) for a plurality of users.

Figure 3:
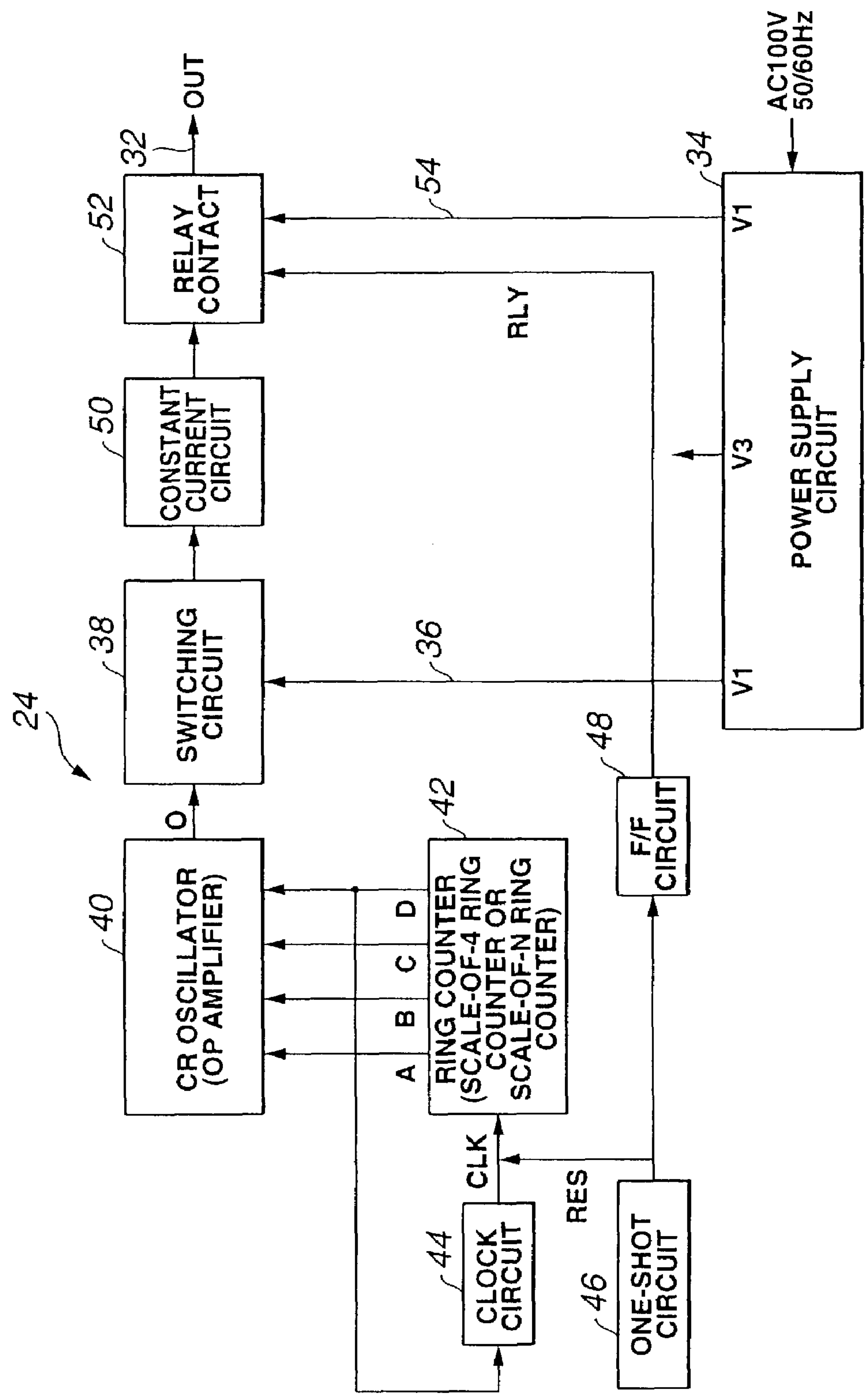
FIG. 3 is a schematic view of a pulse wave output controlling circuit.

FIG. 3 shows the pulse wave output controlling circuit 24, which functions as the pulse wave output controlling unit which is the main control of the control unit 10.

A power supply circuit 34, which is activated by a general commercial power supply (alternate current 100V, 50/60 Hz), outputs respectively different d-c voltages V1, V2 and V3. A power line 36 of V1 is connected to a switching circuit 38. This switching circuit 38 serves to control the on/off switching of a pulse signal from a CR oscillator (OP amplifier) 40.

The CR circuit 40 can output pulse waves of different frequencies depending on changes of contained resistance values. The CR oscillator is connected to a ring counter 42. Although FIG. 3 shows an example of the scale-of-4 counter, it is also possible to apply a scale-of-N counter.

The ring counter 42 of the scale-of-4 counter is operated by a clock signal (CLK) from a clock circuit 44, which signal is inputted after the system is turned on. The ring counter 42 can take out four kinds of outputs (A to D).

The clock signal (CLK) outputted from the clock circuit 44 is reset by a signal D of the ring counter or by a reset signal (RES) from a one-shot circuit 46.

The reset signal (RES) from the one-shot circuit 46 is inputted into a flip-flop circuit (F/F) 48, and an output signal of the F/F circuit 48 is reversed every time the reset signal is inputted. The output signal of the F/F circuit 48 is inputted in a relay contact 52, in which an output signal from the switching circuit 38 is inputted through a constant-current circuit (FET) 50. The relay circuit 52 is connected with a power line 54 of direct current V2 from the power supply circuit 36. The polarity of the pulse wave is reversed by the signal from the F/F circuit 48 to be output to the pair of electrodes 26 and 28. In other words, the pulse wave output controlling circuit 24 generates four kinds of pulse waves, polarities of which can be respectively reversed.

Combination of the pulse waves may be different among users 16. For example, there are cases in which the combination of the pulse waves is made different by switching the frequencies of the pulse waves at certain intervals, or applying pulse waves of different frequencies alternately, or repeating a switching pattern of the polarities of the pulse waves. Moreover, it is also possible to change a pulse width and pulse amplitude accordingly.

The working of the present embodiment will be explained with reference to the timing chart in FIG. 4. When the power supply circuit 34 is turned on, the clock signal (CLK) is outputted from the clock circuit 44, thereby operating the scale-of-4 ring counter 42. By this operation of the scale-of-4 ring counter 42, four kinds of outputs are taken and sent to the CR oscillator 40. Accordingly, the resistance value changes in the CR oscillator and four kinds of frequencies are generated.

The four kinds of frequencies are outputted to the switching circuit 38 in a specified order on the basis of a predetermined pattern, and the on/off control is conducted. Then, at the constant current circuit 50, the currents of the frequencies are controlled to be constant, and then sent to the relay circuit 52. The relay circuit 52 conducts the on/off control of the output of the direct current V2 from the power line 54 on the basis of the inputted frequencies and the output from the relay circuit 52 is sent to the pair of electrodes 26 and 28.

When the ring counter 42 makes one turn, the reset signal (RES) is outputted from the one-shot circuit 46. This reset signal (RES) resets the clock signal, operates the F/F circuit 48, and reverses the output signal (RLY) of the F/F circuit 48.

The reversed output signal is inputted into the relay circuit 52, and it is thereby possible to reverse the polarity of the pulse waves outputted from the relay circuit 52 to the pair of electrodes 26 and 28.

The switching circuit controls the d-c voltage V1, which is to be applied to the constant current circuit with the output of the CR oscillator in order to supply a pulse wave as a final output. The output time of the scale-of-4 ring counter is $T_1$. The frequencies of the pulse waves oscillated from the CR oscillator on the basis of the different outputs (A to D) from the scale-of-4 ring counter, are $f_1$, $f_2$, $f_3$, and $f_4$ respectively. $T_2$ is an output time of the reset signal.

When the pulse waves, the frequencies and polarity of which are changed in a predetermined pattern controlled as above, are supplied to a user, the activity level of the user's brain can be stimulated. For example, if the brain is stimulated by a pulse wave of a specific pattern, it is possible to improve senile dementia, congenital intelligence impairment, or abnormal color sensation. For example, it is possible to bring the intelligence quotient and the learning ability of a Down syndrome patient up to a normal level. It is also possible to prevent a decline in brain functions with advancing age. Moreover, as for a physically unimpaired person, it is possible to quicken the functioning of the brain and to improve the activities of the brain such as memory, judgement, decision, and thinking.

According to the inventor's knowledge, an ear has points leading to each organ of the human body and both ears respectively have points for energization that electrically lead to the neural circuit system of the brain. Accordingly, when the pulse wave is applied to both ears, electricity flows from the right ear through the neural circuit of the brain to the left ear and also from the left ear through the neural circuit to the right ear. When electricity is applied by putting the electrodes, at both ears, it is directly applied to the brain system and the brain functions are activated, thereby improving and preventing the aforementioned statuses. Moreover, it is possible to recover, improve, and enhance the functions of each organ such as internal organs connecting to each point in the both ears.

The pulse wave output controlling circuit can appropriately change the characteristics of the output state of the pulse wave. For example, methods of changing a frequency include: (1) changing the pulse wave frequency from a low frequency to a high frequency; (2) changing the pulse wave frequency from a high frequency to a low frequency; (3) outputting these frequencies alternately. The pulse wave output controlling circuit also changes the polarity of the pulse. It further controls the output time to output the pulse wave of a specific frequency. The characteristics of the output state of the pulse wave are changed by either outputting the pulse wave alone or outputting the combination of the pulse waves.

The methods of changing the output state of the pulse wave will be explained in more detail, again with reference to FIG. 4. In the respective periods of T1, pulse waves of the frequencies $f_1$, $f_2$, $f_3$, and $f_4$ are outputted respectively in a sequential order. At this time, the frequencies are changed in the manner expressed as, for example, $f_1>f_2>f_3>f_4$ or $f_1<f_2<f_3<f_4$. The frequencies may be appropriately changed in the manner expressed as $f_1>f_2>f_3<f_4<f_5$. In FIG. 4, the output period of pulse waves $f_1$ to $f_4$ makes one cycle. Upon the completion of the output of the pulse wave group in one cycle, the polarity of the pulse waves is changed in a sequential order and the pulse waves are continuously outputted. The kinds of pulse waves are not limited to the above examples. The method of changing the frequencies of the pulse waves is not limited to the above example either.

Specifically, the control for changing characteristics and forms of the outputted pulse waves is conducted to output signals which are made by combining pulse waves of different frequencies. The changing control is conducted by making a signal group one set, in which pulse waves of high frequencies and pulse waves of low frequencies are repeated, and after the completion of the output of one set of signals, by changing the polarity of the pulse waves and outputting the signals of the aforementioned set, thereby and outputting the signal groups having different polarities alternately.

Moreover, according to this embodiment explained above, the energization by means of the pulse wave outputs is systematized and plural users under different conditions are divided into respective groups and sorted out into different treatment booths 14 respectively. Accordingly, it is possible to provide treatments simultaneously to a large number of users in different patterns of outputting pulse waves.

The pair of electrodes 26 and 28 may be put not only on the ears, but also on temples or inside the nose, which are the points allowing the pulse waves to be applied directly to the brain. The electrodes may also be placed at asymmetrical positions, for example, by putting one electrode 26 on an ear and the other electrode 28 on the nose.

(Variation)

Figure 5:
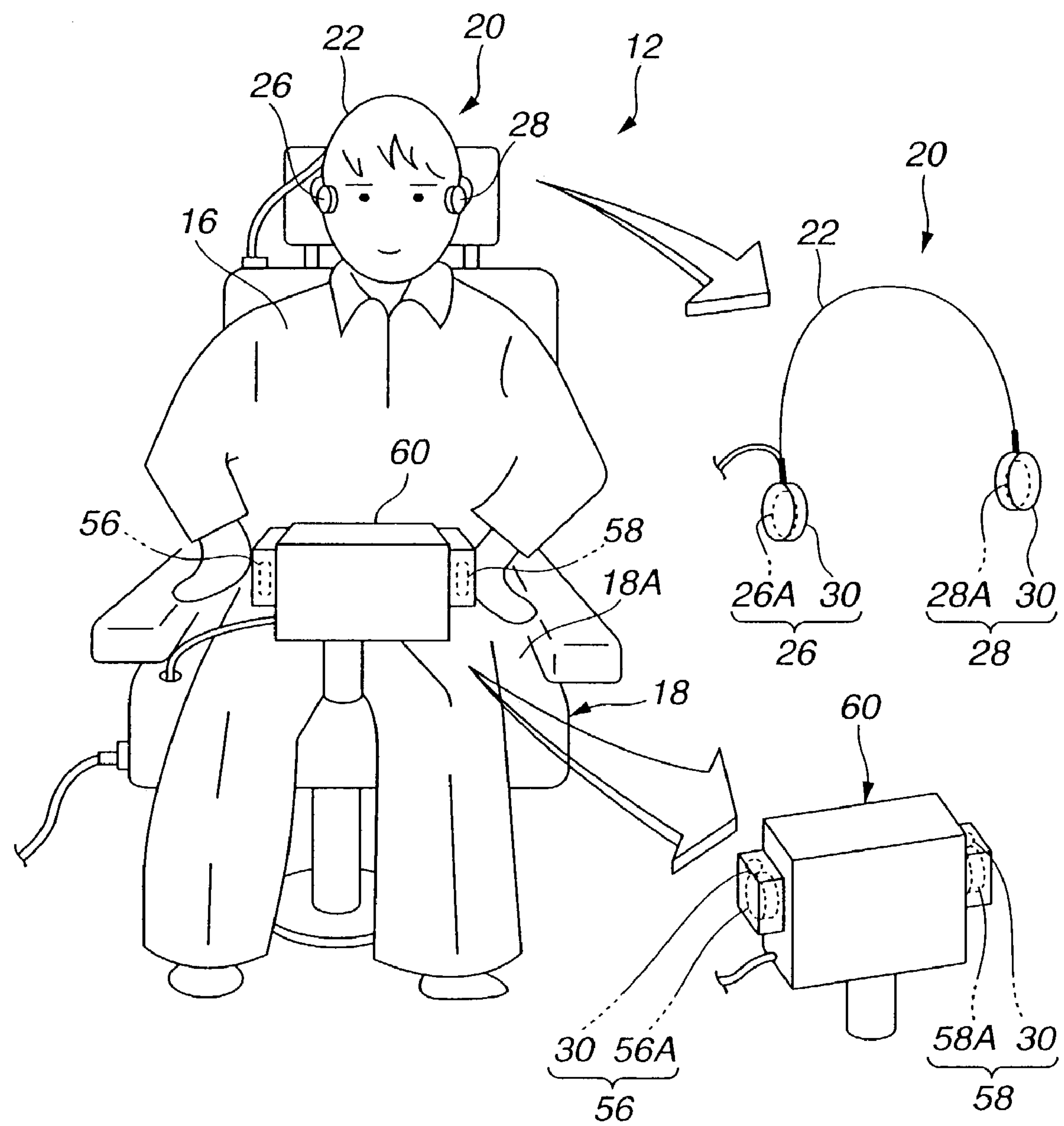
FIG. 5 is a detailed view of a chair 18, which constitutes a part of the treatment table 12 according to a variation of this invention.

In the above embodiment, the pair of electrodes 26 and 28 is put on the ears which the pulse waves are supplied in a predetermined pattern. However, as shown in FIG. 5, it is possible to provide a pair of secondary electrodes 56 and 58 (hereinafter referred to as "subelectrodes 56 and 58") while providing the pair of electrodes 26 and 28 as main electrodes (hereinafter referred to as the "main electrodes 26 and 28").

Specifically, a rectangular guide block 60 is mounted on the treatment table 12 in such a manner that it protrudes upward from a seat member 18A of the chair 18. On both sides of the guide block 60 are mounted sponge members 30 containing the application solution and the pair of the subelectrodes 56 and 58, which are composed of subelectrode agents 56A and 58A made from carbon and contained in the sponge members 30.

The user seated in the chair 18 puts the back of his/her hands on the pair of subelectrodes 56 and 58, thereby receiving the supply of a pulse wave, which is equal to the pulse wave of a specified pattern that is supplied to the pair of main electrodes 26 and 28 placed on the ears.

By supplying the pulse waves both to the ears and to the back of the hands, it is possible to obtain synergistic effects, thereby enabling a quick and more effective therapy.

In this variation, the device and system for supplying the pulse wave are made in a shape of a small box. This box oscillates a specific pulse wave according to instructions from the program which controls the oscillation pattern (pulse wave voltage and current, pulse wave frequency and wavelength, and combinations thereof) of the aforementioned pulse wave and which is stored in the memory inside the box.

Figure 6:
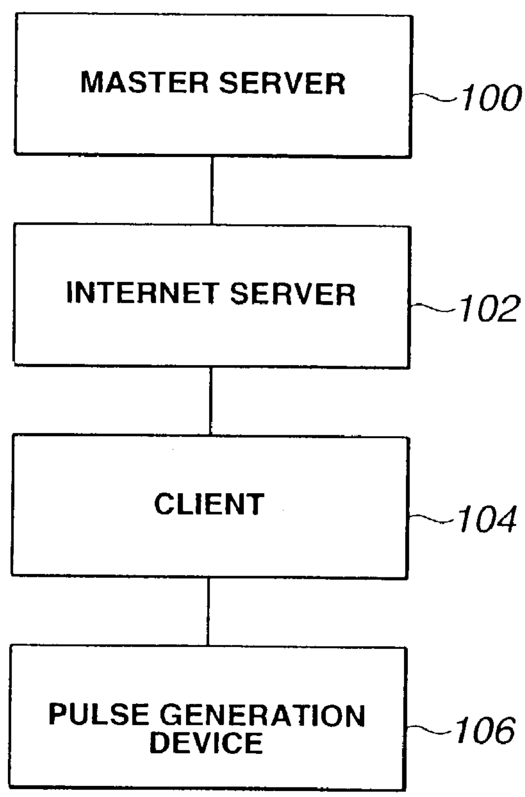
FIG. 6 is a functional block diagram of the pulse wave application system using a communication network.

FIG. 6 is a functional block diagram of a system which implements the pulse oscillation via the Internet. In this system, a master server 100 is connected with an Internet server 102, and the Internet server is connected with a personal computer or an alternative PC unit 104 (such as a home video game machine having a communication function) as a client. Each client is connected with a pulse generation device. The pulse generation device is shown in FIG. 3 as already described above. To this pulse generation device, the four kinds of output signals A to D shown in FIG. 3 are transmitted from the client.

Figure 7:
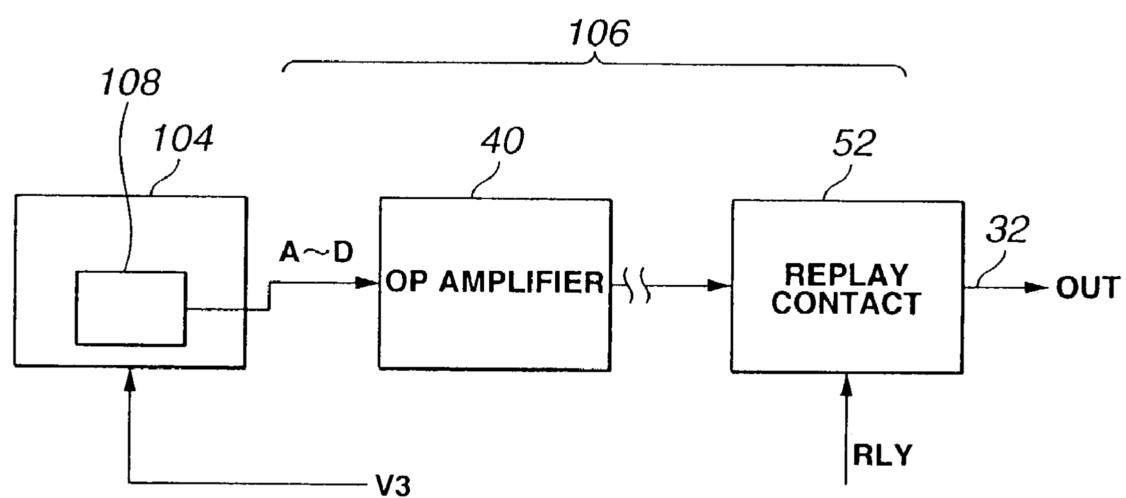
FIG. 7 is a block diagram showing the connection of the client with the pulse wave generation device.

FIG. 7 is a functional block diagram of the client 104 and the pulse generation device 106. Pulse wave signals (for example, A to D in FIG. 3) generated at the pulse generation unit 108 within the personal computer are transmitted to the OP amplifier 40. This pulse generation unit 108 is composed of a CPU and a buffer circuit, and is supplied with necessary electricity from the power supply circuit ($V_3$). A reversed signal (RLY) is outputted from the pulse generation unit 108 within the client to the relay contact 52.

The master server 100 implements control processing necessary for each client to operate the system as illustrated in to FIGS. 6 and 7. The Internet server 102 functions as a certificate server and controls the transmission of data and programs between the master server 100 and the respective clients 104 and the billing for the respective clients.

This operation will be hereinafter explained in the order of events. Explained first is a case in which the user accesses the master server for the first time. The user either accesses a homepage of a manager who manages the master server, or downloads from memory media such as CDs into a client, a connection program to the master server or an operation system program for operating the system in FIG. 7.

Next, the master server newly registers the user's ID, password, and account in the certificate server. Subsequently, when the user accesses the master server, the master server makes inquiries to the certificate server about the ID and the password and decides whether or not the user is registered. The master server also makes inquiries to the certificate server about the account situation and decides whether or not it is possible to connect the client to the master server. If it is decided that the client can be connected to the master server, the aforementioned OS program is activated.

First, the master server requires the client to make preparations necessary for conducting the pulse application. Examples of such preparations include turning on the pulse generation device, connecting the application electrodes to the pulse generation device, and putting the electrodes on the user's ears.

Next, when the user notifies the master server of the completion of all preparations and of the pulse application start request, the master server sends to the client a pulse wave generation control signal according to the operating system. The client generates the aforementioned pulse waves (A to D in FIG. 3) on the basis of the control signal. The master server sends the control signal to the client for a specified period of time. After the specified period of time had elapsed, the master server completes the sending of the control signal and notifies the client of the completion of the pulse wave generation.

The master server can provide the client with sound information such as music and English conversations or image information, during the pulse wave generation period. While the pulse wave is being applied to the user, the user's sensibility to the external stimulation information increases and the information acquiring ability enhances. The necessary sound information can be provided from the client to speakers by arranging the waterproof speakers at positions on the electrode devices where they contact the ears and by connecting the ends of the waterproof speakers to the client.

Even after the client downloaded from the master server a file of the pulse wave generation control signal and the connection by the client to the server was cut off by the downloaded control signal file, it is possible to make the pulse generation device generate a pulse for a specified period of time. After the specified period of time had elapsed, the OS program deletes the control signal file.

It is possible to set plural patterns of the pulse wave generation control signal according to the status of the user. It is also possible to cause the master server to make inquiries to the respective users about their physical conditions and symptoms and to transmit to the client the pulse wave control signals having the necessary wave forms and frequencies according to the physical conditions of the users.

According to this variation, a desirable pulse signal for treating human bodies can be outputted from each client by means of the program obtained via the network. In the above example, the control program is supplied to the communication terminal by using a communication unit. However, it is possible to download, into the memory device of a microcomputer, the control program stored in various kinds of non-communication media such as CDs, MDs, FDs, and DVDs instead of the communication media and the carrier wave media on the communication network. Moreover, the microcomputer may be integrated with the box comprising the pulse wave output controlling circuit.

"The Case of Boys in the Lower Grades of Elementary School"

Figure 4:
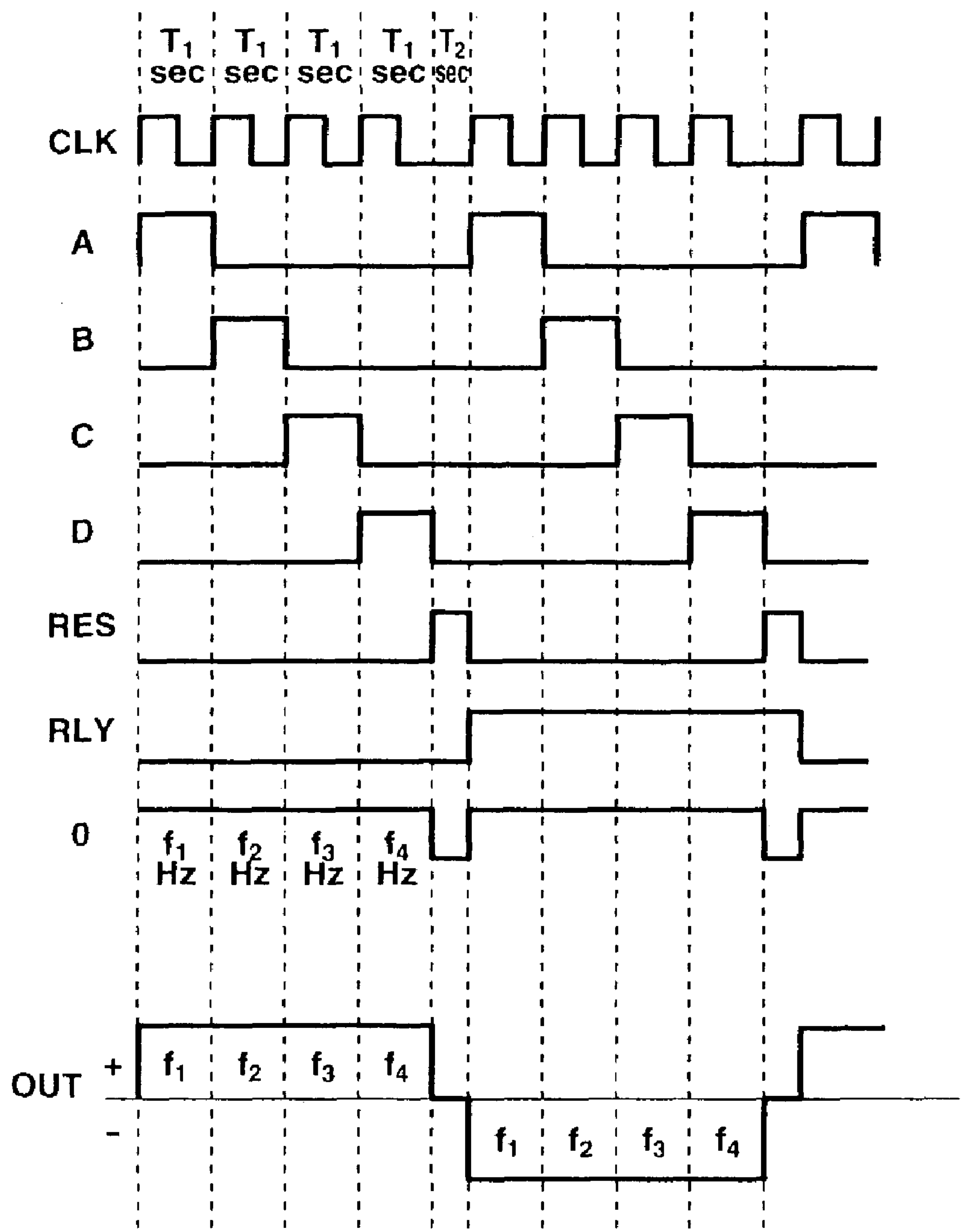
FIG. 4 is a timing chart according to the embodiment of this invention.

The pulse waves of the pattern shown in FIG. 4 were applied dozens of times in total to three patients who had serious abnormal color sensations. The pulse wave application was conducted once a day, 2 to 3 times a week. The pair of the electrodes was put on the respective ears and the application was conducted for an hour at a time. A test using a color vision testing table revealed that each patient who had serious abnormal color sensation before the application, had his color vision finally improved to the level of a physically unimpaired person.

"The Case of Girls in the Lower Grades of Elementary School"

The pulse application was conducted for several years on a Down syndrome patient. The application method of the pulse wave was the same as in the case of the abnormal color sensations. The intelligence quotient of the patient finally rose to the level equivalent to that of a physically unimpaired person.

By providing the pulse waves of a predetermined pattern based on the results of many years of study by the applicant, to the head of the human body in order to stimulate the brain directly, it is possible to improve or activate the functioning of the brain. This system allows pulse waves to be provided to a large number of users in respectively different patterns, and it enables a quick, reliable application treatment. Moreover, the use of the head set 20 frees the user's hands. Accordingly, stimulation can also be given to the back of their hands by means of the pulse waves, thereby obtaining synergistic effects with the pulse wave supplied to the ears.

In the above embodiment and the variation, explanations were given about the hardware structure as the pulse wave output controlling circuit 24. However, it is possible to use software to control the pulse generation and the polarity by storing in the software a program for generating pulse waves and changing the polarity of the pulse waves.

INDUSTRIAL APPLICABILITY

As explained above, according to this invention, it is possible to provide an application system for a human body, which enables enhancement, improvement, and amelioration of the comprehensive activity level of the cranial nerve and the central nervous system.

It is also possible to provide an application system for a human body, which enables improvement of the abnormal color sensation as well as improvement of and recovery from the senile dementia and congenital intelligence impairment.

Moreover, it is possible to provide an application system, which enables enhancement of mental activity and intelligence level, such as EQ and IQ, of even a physically unimpaired person. Furthermore, it is possible to provide a system which achieves activation of the entire nervous system of the human body.

What is claimed is:

1. A pulse wave application system for applying a pulse wave to a human body, comprising:

a pulse wave output controlling unit for generating a pulse wave signal and changing characteristics of the generated pulse wave signal periodically; and a pair of electrode units, to which the pulse wave signal is supplied, wherein the electrode units include electrodes adapted to be worn on the head of the human body to apply the pulse wave to the human body, the electrodes being structured in such a manner that they can be put on the ears of the human body, and wherein the pulse wave output controlling unit outputs the pulse wave signal to the electrode units by changing its output pattern according to a sequence of the following order:

a pulse wave being output with a relatively high frequency pulse wave and a relatively low frequency pulse wave alternating;

a pulse wave being output with its frequency gradually increasing;

a pulse wave being output with its frequency gradually decreasing;

a pulse wave being output with an output state repeated periodically; and a pulse wave being output with its polarity changed periodically.

2. A pulse wave application system, according to claim 1, wherein a client connected to a communication network is provided with the pulse wave output controlling unit, and the controlling unit outputs a pulse wave signal on the basis of a control signal supplied from a server to the client.

3. A pulse wave application system for applying a pulse wave to a human body, comprising:

a pair of electrode means for providing a pulse wave signal, said electrode means are adapted to be mounted on the head of a human body to apply the pulse wave to the human body;

a power supply circuit, providing voltages V1 and V2 to a switch circuit and a delay circuit respectively;

a pulse wave output controlling means for generating the pulse wave signal and changing characteristics of the generated pulse wave signal periodically, the pulse wave output controlling means comprising:

a CR oscillator, which outputs pulse wave signals of different frequencies to the switch circuit based on a variation of the value of a built-in resistor, the switch circuit keeping the signal constant and then inputting it to the delay circuit;

a ring counter, which acts according to a clock signal output from a clock circuit, thereby outputting four types of signals to the CR oscillator;

a bistable multivibrator, which reverses the output signal based on a reset signal from a one flip-flop circuit, and inputs the reversed signal to the delay circuit;

wherein said clock signal is reset based on a signal from the ring counter or a reset signal from the one flip-flop circuit.

4. The system of claim 3, wherein the electrode means are configured to be mounted on the ears of the head of a human body.

5. The system of claim 4, wherein the pulse wave output controlling means alternately outputs a pulse wave of a higher frequency and a pulse wave of a lower frequency, or outputs the pulse wave with the frequency gradually increasing or decreasing, while repeating periodically the output state of the pulse wave and varying the polarity of the pulse wave within each period.

6. The system of claim 4, wherein the pulse wave output controlling means is positioned in a client connected to a communication network, and outputs the pulse signal based on a controlling signal provided by a server to the client.

7. The system of claim 3, wherein the pulse wave output controlling means alternately outputs a pulse wave of a higher frequency and a pulse wave of a lower frequency, or outputs the pulse wave with the frequency gradually increasing or decreasing, while repeating periodically the output state of the pulse wave and varying the polarity of the pulse wave within each period.

8. The system of claim 3, wherein the pulse wave output controlling means is positioned in a client connected to a communication network, and outputs the pulse signal based on a controlling signal provided by a server to the client.

* * * * *